(12) United States Patent
Talbiersky et al.

(10) Patent No.: US 6,258,985 B1
(45) Date of Patent: Jul. 10, 2001

(54) METHOD FOR REMOVING METAL IONS FROM CRESOL MIXTURES

(75) Inventors: Jörg Talbiersky, Dorsten; Edgar Fuhrmann; Wolfgang Brüggemann, both of Castrop-Rauxel, all of (DE)

(73) Assignee: Rütgers VFT AG, Castrop-Rauxel (DE)

( * ) Notice: Subject to any disclaimer, the term of this patent is extended or adjusted under 35 U.S.C. 154(b) by 0 days.

(21) Appl. No.: 09/424,524
(22) PCT Filed: Mar. 30, 1999
(86) PCT No.: PCT/EP99/02191
  § 371 Date: Nov. 23, 1999
  § 102(e) Date: Nov. 23, 1999
(87) PCT Pub. No.: WO99/50212
  PCT Pub. Date: Oct. 7, 1999

(30) Foreign Application Priority Data

Apr. 1, 1998 (DE) .............................. 198 14 555

(51) Int. Cl.$^7$ ...................... C07C 37/68
(52) U.S. Cl. ............................ 568/749; 568/758
(58) Field of Search ...................... 568/749, 758

(56) References Cited

U.S. PATENT DOCUMENTS 3,351,669 * 11/1967 Anderson ........................ 568/749
4,365,099   12/1982 Faler et al. .

\* cited by examiner

*Primary Examiner*—Michael L. Shippen
(74) *Attorney, Agent, or Firm*—Amster, Rothstein & Ebenstein

(57) ABSTRACT

A method for removing of metal ions from cresol or from mixtures of aromatic compounds containing cresol is disclosed, wherein the water content in the cresol mixture is adjusted to at least about 0.5 per cent by weight by the addition of water and the water-and-cresol mixture is subsequently passed over an acid ion exchanger. As a result of this process a metal ion content of less than 20 ppb per metal ion is achieved.

4 Claims, No Drawings

METHOD FOR REMOVING METAL IONS FROM CRESOL MIXTURES

The present invention relates to a method for removing metal ions from cresol or from mixtures of aromatic compounds containing cresol.

Cresol mixtures are isomer mixtures of o-, m- and p-cresol (methylphenol). They are obtained, among others, as a product in the distillation of coaltar. Depending on the production and storage method, cresol mixtures may contain more or less large quantities of metal ions as contaminants. Thus, a typical cresol mixture obtained from the distillation of coaltar usually contains about 30 to 70 ppb (1 ppb=1 mg/t) of sodium, about 20 to 40 ppb of iron and about 1 to 10 ppb of chromium.

Such metal ion contaminants are problematic, for example, in the use of cresol as a monomer to produce cresol resins for the microchip industry. The metal ion concentration in the cresol mixtures required for this purpose may not exceed 20 ppb per metal ion.

Consequently, it is an object of the present invention to provide a method for removing metal ions from cresol mixtures through which metal ion concentrations in the cresol mixture are reduced to <20 ppb per metal ion. It is a further object of the present invention that the method be simple and inexpensive.

These objects are achieved in such a way that in a cresol mixture or a phenolic mixture containing cresol a water content of at least about 0.5 per cent by weight is adjusted by the addition of water and, subsequently, the cresol-and-water mixture is passed over an acidic ion exchanger.

The process according to the present invention is particularly suitable for the purification of cresol or aromatic mixtures containing cresols that contain a starting concentration of metal ions of about 0,01 to 0,1 ppm (10 to 100 ppb) per metal ion.

In addition to the desired reduction of the metal ion concentration the method in accordance with the invention comes with the further advantage that it considerably reduces the concentration of any bases such as pyridine, aniline and quinoline that may be contained in the cresol mixture. In order to reduce the contamination by metal ions the distillation of the cresol mixtures has also been considered. However, distillation has proven to be disadvantageous because it causes a shift in the quantity shares of the components of the cresol mixture. Moreover, the reduction of the metal ion concentration was considerably less effective.

It has been seen that untreated cresol mixtures quickly render the ion exchanger useless for the removal of metal ions in the ppb range. Surprisingly it was noticed that this problem did not occur after the addition of small quantities of water to the cresol mixture. In fact, after the addition of small quantities of water the ion exchanger remained active even after a long period of time. In accordance with a preferred embodiment of the invention the water content in the cresol mixtures, particularly when the same is to be used as starting material for polymers in the microchip industry, is adjusted to up to about 15 per cent by weight, particularly up to about 10 per cent by weight or about 1 to 5 per cent by weight of water relating to the weight of the cresol mixture or the aromatic mixture containing cresol.

In accordance with the present invention, any kind of acidic ion exchanger can be used. According to a preferred embodiment of the present invention, strongly acidic ion exchangers, such as ion exchange resins on the basis of a styrene/divinylbenzene copolymer, are used. The use of strongly acidic ion exchangers proves particularly advantageous for the removal of such ions that are difficult to remove by conventional methods, e.g. $Na^+$ ions. The ion exchange resins preferably have a macroporous structure and/or a high degree of cross linking of the polymer matrix.

As an example for an ion exchanger that is particularly preferred in the process according to the present invention, the ion exchange resin Amberlyst® 15 (Rohm & Haas Company) may be mentioned. Amberlyst® 15 is a strongly acidic, macroporous ion exchange resin on the basis of a styrene/divinylbenzene copolymer with a divinylbenzene content of about 20% and a —$SO_3H$ group concentration (active groups) of about 4.7 eq/kg. Amberlyst® 15 has a catalyst surface of about 45 $m^2$/g, a water content of about 51 to 56% and a bulk density of about 770 g/l.

As is common in reactions of this kind, the acidic ion exchangers are activated prior to initial operation by treatment with acids such as sulphuric acid. The ion exchanger is usually washed with distilled water before and after the activation with acid. It is advantageous not to dry the ion exchanger with methanol or similar solvents after the washing with distilled water.

The quantity of the ion exchanger and the flow speed generally depend on the degree of contamination of the cresol mixture to be purified. In a case where the degree of contamination of the cresol mixture is high it will be necessary to employ a larger quantity of the ion exchanger and/or a lower flow speed than in a case where the degree of contamination is low. However, as a rule of thumb, it was found that it is appropriate to use 1 kg of ion exchanger for each 100 kg of starting material. After a certain flow volume it is necessary to regenerate the ion exchanger by the methods commonly known in the art.

The temperature at which the method in accordance with the present invention is practiced is uncritical. It is mainly necessary to avoid additional energy costs, which is why ambient temperature will mostly be chosen.

The product of the method according to the present invention is a cresol mixture which may contain phenol and further alkylated aromatics, and particularly shows a metal ion content of less than 20 ppb per metal ion. The water quantity contained in the product mixture corresponds to the water quantity adjusted in the starting material prior to the flow through the ion exchanger.

The invention will now be explained in closer detail by reference to specific embodiments.

EXAMPLE 1

A cresol mixture obtained from the coaltar distillation having an Na ion concentration of 70 ppb and an Fe ion concentration of 21 ppb was mixed with 10 per cent by weight of distilled water and passed at a flow speed of 400 ml/h through a continuous-flow reactor of the size of 38×180 mm which was filled with 150 g of an ion exchanger of the type Amberlyst® 15 H (weight when dry: 89.1 g) previously treated successively with 1 l of water, 2 l of sulphuric acid (12%) and 1 l of water. Up to a quantity of flow of 10,000 ml the cresol mixture passed over the ion exchanger showed metal ion contents of c(Na) 8 ppb and c(Fe)<10 ppb. After a quantity of flow of 20,000 ml the metal ion contents were c(Na) 16 ppb and c(Fe)<10 ppb.

EXAMPLE 2

A cresol mixture obtained from the coaltar distillation with an Na ion concentration of 26 ppb, an Fe ion concentration of 22 ppb and a base concentration of 85 ppm was passed, as in example 1, through the Amberlyst® 15 ion exchanger, but without any prior addition of water. Following a quantity of flow of approx. 2,500 ml the cresol mixture passed over the ion exchanger showed contents of c(Na) 7 ppb and c(Fe)<10 ppb and c(base) 8 ppm. Following a quantity of flow of approx. 11,000 ml the cresol mixture again showed clearly higher metal ion concentrations of c(Na) 11 ppb and c(Fe) 21 ppb. This indicates a rapid consumption of the ion exchanger under water-free conditions. Following a quantity of flow of approx. 10,000 ml an increase of the sodium and base concentrations was again noticed with c(Na) 19 ppb and c(base) 12 ppm. Following a quantity of flow of 12,500 ml the sodium concentration, with c(Na) 22 ppb, exceeded the top threshold permitted for the use in the production of microchips, with the Fe and base concentrations having been c(Fe) 12 ppb and c(base) 12 ppm after this quantity of flow. This indicates a rapid consumption of the ion exchanger under water-free conditions.

What is claimed is:

1. A method for removing metal ions from cresol or from mixtures of aromatic compounds containing cresol, wherein the water content of the cresol mixture is adjusted to at least about 0.5 per cent by weight by the addition of water and the cresol-and-water mixture is thereafter passed over an acidic ion exchanger.

2. A method as claimed in claim 1, wherein the water content of the cresol mixture is adjusted to about 1 to 10 per cent by weight.

3. A method as claimed in claim 1, wherein the ion exchanger is strongly acidic.

4. A method as claimed in claim 2, wherein the ion exchanger is strongly acidic.

* * * * *